US012661467B2

(12) United States Patent
Zarembo et al.

(10) Patent No.: US 12,661,467 B2
(45) Date of Patent: Jun. 23, 2026

(54) MEDICO-SURGICAL TUBES

(71) Applicant: SMITHS MEDICAL INTERNATIONAL LIMITED, Ashford (GB)

(72) Inventors: John Zarembo, Minneapolis, MN (US); Eli Joseph McElwain, Champlin, MN (US); Mark Henry Faust, Stacy, MN (US); Mary Schueppert, Minneapolis, MN (US)

(73) Assignee: ICU MEDICAL INTERNATIONAL LIMITED, Ashford (GB)

( * ) Notice: Subject to any disclaimer, the term of this patent is extended or adjusted under 35 U.S.C. 154(b) by 592 days.

(21) Appl. No.: 18/012,717

(22) PCT Filed: Jul. 14, 2021

(86) PCT No.: PCT/GB2021/000083
§ 371 (c)(1),
(2) Date: Dec. 23, 2022

(87) PCT Pub. No.: WO2022/018394
PCT Pub. Date: Jan. 27, 2022

(65) Prior Publication Data
US 2023/0293837 A1　　Sep. 21, 2023

(30) Foreign Application Priority Data
Jul. 23, 2020　(GB) ..................................... 2011418

(51) Int. Cl.
*A61M 16/04*　　(2006.01)
*A61M 25/00*　　(2006.01)

(52) U.S. Cl.
CPC .... *A61M 16/0425* (2014.02); *A61M 16/0434* (2013.01); *A61M 16/0486* (2014.02); *A61M 25/0052* (2013.01)

(58) Field of Classification Search
CPC .. A61M 16/0425; A61M 25/005–0053; A61M 16/0418
See application file for complete search history.

(56) References Cited

U.S. PATENT DOCUMENTS

| | | | |
|---|---|---|---|
| 2002/0195110 A1* | 12/2002 | Watton | ..... A61M 16/0418 128/207.15 |
| 2014/0236122 A1* | 8/2014 | Anderson | ..... A61M 25/0012 604/523 |

(Continued)

FOREIGN PATENT DOCUMENTS

| | | |
|---|---|---|
| DE | 102008015050 A1 | 9/2009 |
| GB | 2552250 A | 1/2018 |

(Continued)

OTHER PUBLICATIONS

PCT International Search Report for PCT/GB2021/000083 dated Nov. 11, 2021.
PCT Written Opinion for PCT/GB2021/00083 dated Nov. 11, 2021.

*Primary Examiner* — Bradley H Philips
(74) *Attorney, Agent, or Firm* — Louis Woo

(57) ABSTRACT
A cuffed tracheostomy tube has a shaft (10) with an inflation lumen (16) extending longitudinally along the shaft and opening at its patient end into a sealing cuff (13). The tube also includes a reinforcement member provided by a metal wire (25) wound into two sets of loops (26A) and (26B) of different widths. The loops (26) extend part way around the shaft (10) up to but without crossing the inflation lumen (16).

7 Claims, 3 Drawing Sheets

(56) References Cited

U.S. PATENT DOCUMENTS

| | | | | |
|---|---|---|---|---|
| 2016/0030711 A1* | 2/2016 | Coppi | ............... | A61M 25/0052 |
| | | | | 604/526 |
| 2017/0173286 A1* | 6/2017 | Bateman | ........... | A61M 16/0434 |
| 2020/0054860 A1 | 2/2020 | McElhaney et al. | | |
| 2023/0137005 A1* | 5/2023 | Quackenbush | ... | A61M 16/0434 |
| | | | | 128/207.14 |

FOREIGN PATENT DOCUMENTS

| | | | | |
|---|---|---|---|---|
| JP | H067450 A | 1/1994 | | |
| WO | WO-2009115403 A1 * | 9/2009 | ........ | A61M 16/0465 |
| WO | 2015075412 A1 | 5/2015 | | |
| WO | WO-2017189364 A1 * | 11/2017 | ............... | A61F 2/06 |

* cited by examiner

MEDICO-SURGICAL TUBES

This invention relates to medico-surgical tubes of the kind including a shaft, and an elongate member extending along the shaft within its wall along a substantially straight line extending parallel to the axis of the shaft, the tube also including a reinforcement member extending along a part at least of the length of the shaft.

Tracheal tubes are used to enable ventilation, respiration, or spontaneous breathing of a patient. Tracheostomy tubes are inserted into the trachea via a surgically formed opening in the neck so that one end locates in the trachea and the other end locates outside the patient adjacent the neck surface. Tracheostomy tubes can be inserted by different techniques, such as the surgical cut-down procedure carried out in an operating theatre or a cricothyroidotomy procedure, which may be carried out in emergency situations.

Tracheostomy tubes are generally used for more long-term ventilation or where it is not possible to insert an airway through the mouth or nose. The patient is often conscious while breathing through a tracheostomy tube, which may be open to atmosphere or connected by tubing to some form of ventilator. The tube is secured in position by means of a flange fixed with the machine end of the tube and positioned to extend outwardly on opposite sides of the tube. The anatomy of patients varies considerably according to age and build.

Tracheostomy tubes can be made of various materials and are usually of a bendable plastics material such as PVC, polyurethane, or silicone. Silicone tubes are particularly advantageous for long-term use because they can be highly flexible, making them less traumatic and damaging to tissue contacted by the tube. The soft nature of silicone, however, means that they can be easily kinked and occluded by external pressure unless measures are taken to avoid this. Often, silicone tubes are reinforced by means of a stiff helical member extending along the tube. Typically, the reinforcement member is a metal wire. Tracheostomy tubes are often also provided with an inflatable sealing cuff that is inflated around the tube towards its patient end in order to form a seal with the trachea so that gas is confined to flow along the bore of the tube. The sealing cuff is inflated via an inflation lumen extending along the tube. If the tube is reinforced, the inflation line cannot extend within the thickness of the wall of the tube so extends along the outside of the reinforcement wire. This leads to a protruding ridge extending along the length of the outside of the tube. The problem with this is that the protruding ridge interrupts the smooth outer surface of the tube and can cause discomfort or trauma to tissue in the region of the stoma and the trachea. This can be a particular problem with tubes intended for paediatric and neonatal use. The same problem exists in uncuffed tubes having other elongate members extending along their length, such as a suction or gas-sampling lumen, or a cable or wire.

It has been proposed in GB933307 to incorporate a helical inflation line within the thickness of the wall of the tube to serve the dual purposes of both enabling inflation gas to be supplied to the sealing cuff and acting as a helical reinforcement member. GB2552250 describes a tube having a separate helical reinforcing wire and inflation line wound parallel to the reinforcement. The problem with these arrangements is that, in order to achieve sufficient reinforcement, the inflation line must be wound with a very close pitch, leading to a large number of turns and a large overall length. The long length of the inflation line gives it a high resistance to gas flow along it, making it difficult to inflate and deflate the sealing cuff. This problem is even worse with tubes, such as those with a silicone cuff, that are inflated using a liquid.

It is an object of the present invention to provide an alternative medico-surgical tube.

According to the present invention there is provided a medico-surgical tube of the above-specified kind, characterised in that the reinforcement member has portions extending around the shaft, and that the portions extend up to but without crossing the elongate member.

The portions of the reinforcement member are preferably a plurality of loops extending around a part of the circumference of the shaft. The reinforcement member may include two sets of loops extending around the shaft in opposite senses and extending up to the elongate member from opposite sides. The loops of one set are preferably wider than the loops of the other set. The reinforcement member may be of a metal wire. The wall of the shaft may be of silicone. The tube may include an inflatable cuff towards its patient end, the elongate member being an inflation lumen opening into the cuff at one end. The tube is preferably a tracheal tube, the inflatable cuff being a sealing cuff.

A tracheostomy tube according to the present invention will now be described, by way of example, with reference to the accompanying drawings in which.

Figure 1:
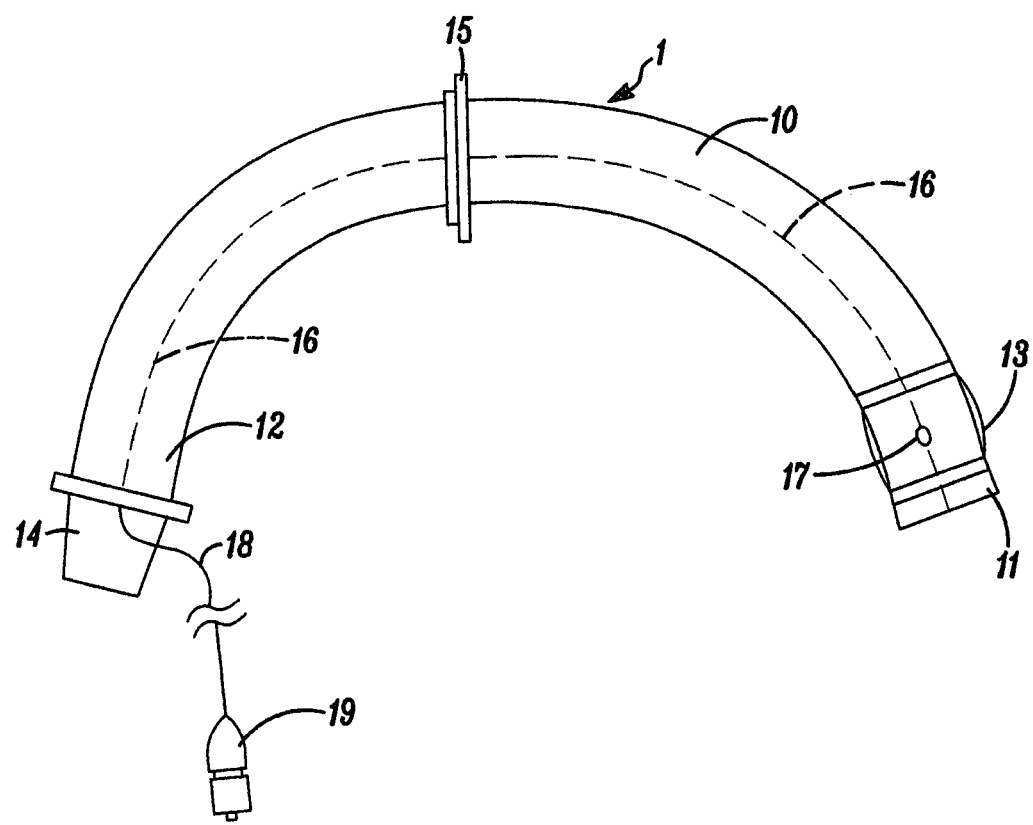
FIG. 1 is a side elevation view of the tracheostomy tube.

With reference first to FIG. 1, the tracheostomy tube 1 has a generally curved shaft 10 of circular section with a forward, distal patient end 11 and a rear, proximal machine end 12. The patient end 11 is adapted to be located within the trachea of the patient and the machine end 11 is adapted to extend through the tracheostomy stoma and to be located externally of the patient. Towards its patient end 11 the shaft 10 supports a conventional sealing cuff 13 of a high pressure kind made of an elastic material that lies close to the shaft 10 when deflated and is stretched outwardly when inflated. The shaft 10 and cuff 13 are both formed of a soft silicone material and the shaft is reinforced along its length by a reinforcement element that will be described in detail later. The machine end 12 of the shaft 10 is terminated by a conventional male tapered connector 14 adapted to make a gas-tight connection in a mating female tapered connector (not shown) at one end of ventilation tubing, or to be left open when the patient is breathing spontaneously. The tube 1 is shown as having a radially extending neck flange 15 spaced forwardly of the connector 14, to which a neck tie or strap (not shown) can be fastened in order to secure the tube with the patient's neck. This construction allows for a short length of the shaft 10 to project outwardly beyond the flange 15. In alternative tubes the shaft could be shorter, and the connector located directly at the flange so that tube does not project substantially out of the patient. The tube also includes an inflation lumen 16 extending along one side of the shaft 10 and opening towards its patient end 17 under and into the interior of the cuff 13. Adjacent the machine end connector 14 the inflation lumen 16 is joined with one end of a small-bore inflation tube 18 the other end of which is connected to a combined inflation indicator and valve 19. It will be appreciated that the tube could be of a different size, shape and material according to the application.

Figure 2:
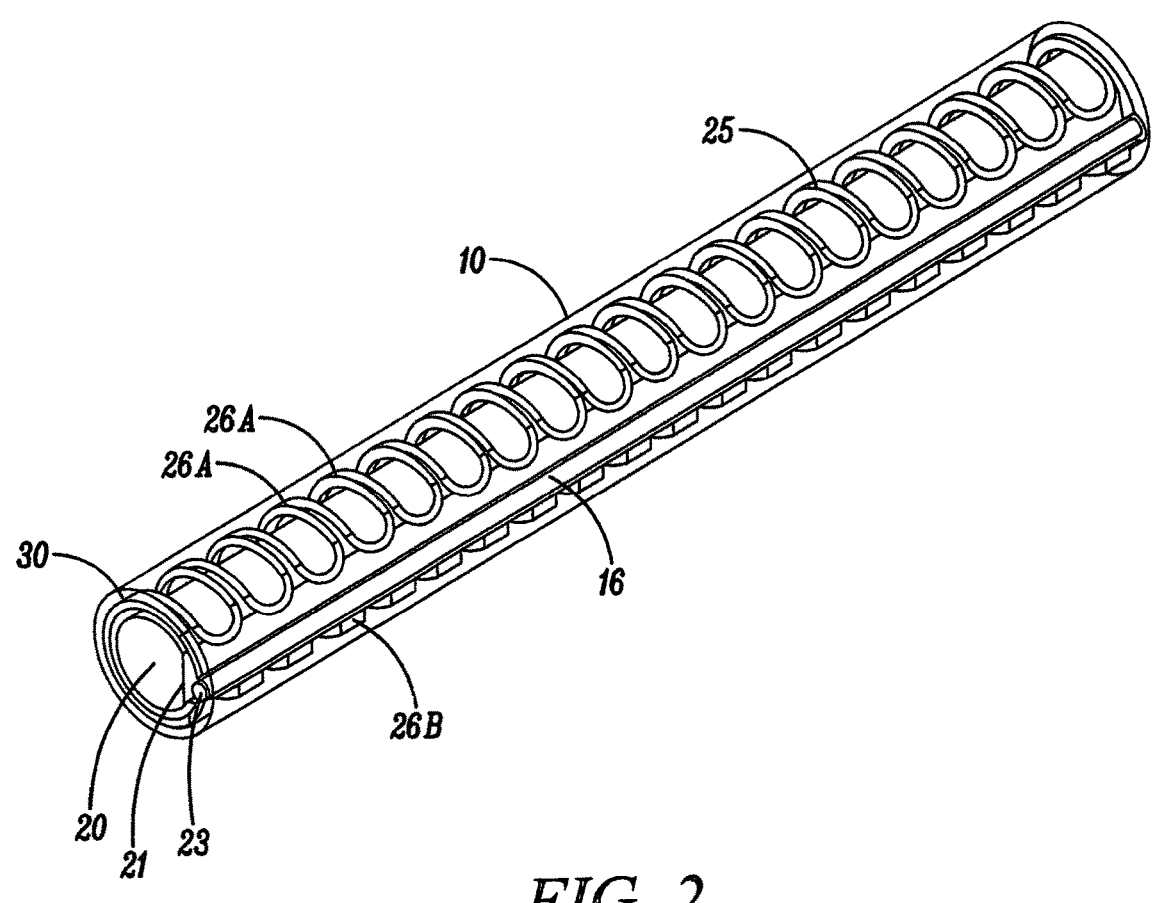
FIG. 2 is perspective phantom drawing of the shaft of the tube.
Figure 3:
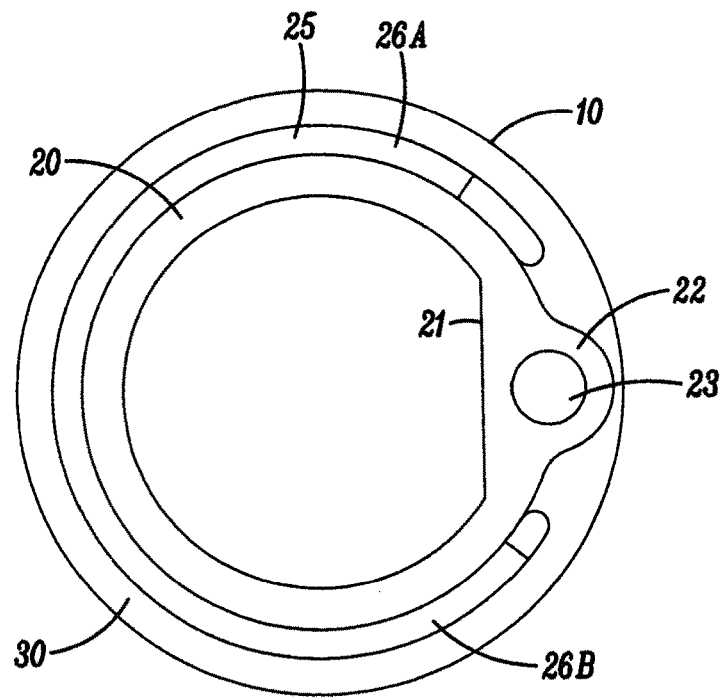
FIG. 3 is a cross-sectional transverse view of the shaft.
Figure 4:
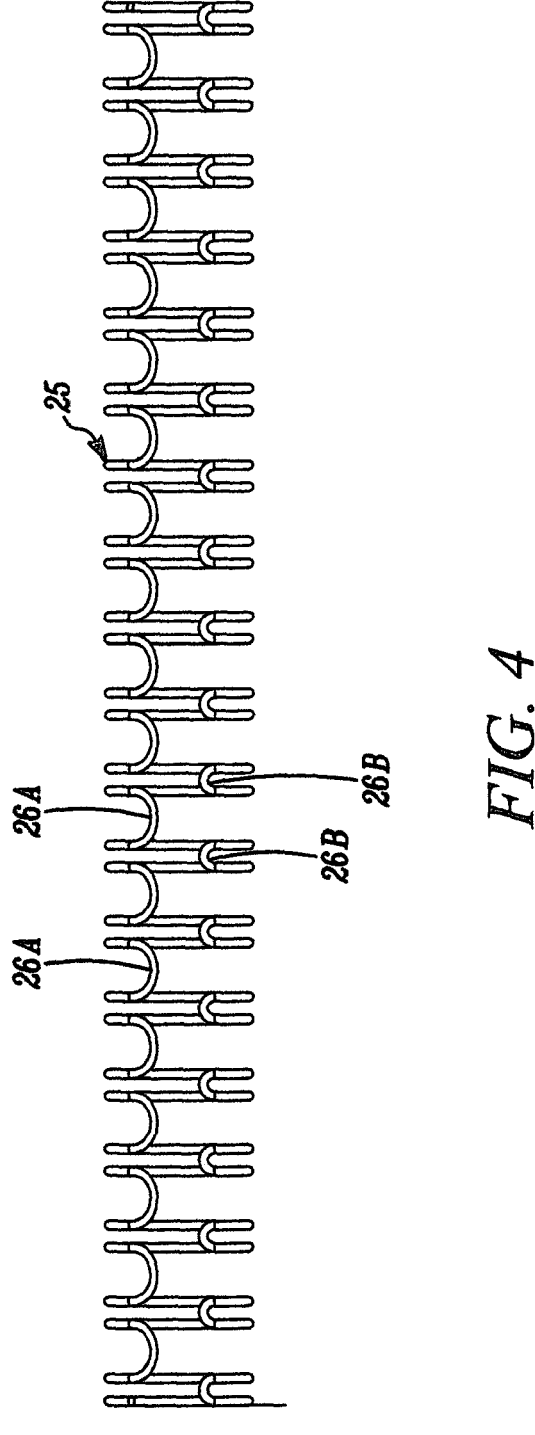
FIG. 4 is a side elevation view of the reinforcement member before assembly on the shaft.

The construction of the shaft 10 is shown in more detail with reference to FIGS. 2 to 4. The shaft 10 has an inner layer 20 of silicone of a generally cylindrical shape the wall of which is thickened along one side by an internal flat 21 and an external rib 22 of semi-circular section. The inner layer 20 could be formed by any conventional technique such as extrusion, moulding or dipping. Within the rib 22 extends a bore 23 of circular section that provides the inflation lumen 16. The bore 23 need not have a circular section but could be other shapes, such as oval. A reinforcement member or element 25 extends along the outside of the inner layer 20 having portions extending around the shaft 10 up to, that is, close to but not crossing the inflation lumen 16. The reinforcement element 25 takes the form of a single, continuous element such as a resilient metal wire, such as of stainless steel, Nitinol, NP35N or the like, of circular section. The element 25 is wound back and fore around the inner layer 20 in a boustrophedon, serpentine or zig-zag fashion where the portions extending around the shaft are formed into part-circumferential loops 26 spaced from one another along the length of the shaft 10. A set of loops 26A formed in one direction are wider than a set of loops 26B formed in the opposite direction, typically being about three times as wide. The closed ends of the loops 26A and 26B extend up to and close to the inflation lumen 16 from opposite sides, leaving a longitudinal gap between the two sets of loops along the shaft 10. The reinforcement member 25 may be preformed and slid onto the inner layer 20 from one end. Alternatively, the reinforcing member 25 could be opened by separating the two sets of loops 26A and 26 B from one another so that it can be loaded sideways onto the inner layer 20, the resilience of the reinforcing member causing it to contract about the inner layer when it is released. The wire need not have a circular section, but it could instead have a flattened profile, being wider in a cylindrical plane coaxial with the axis of the shaft 10. The reinforcement need not be a metal wire but could, for example, be a filament of a stiff plastics, ceramic, or glass fibre so as to enable the tube to be made compatible with MRI scanning. The reinforcement could alternatively be in the form of a planar sheet of a stiff material cut or otherwise formed into a series of annular strips. Such strips could be in the form of a continuous loop but could alternatively be in the form of separate ribs extending outwardly from a common spine around the shaft as far as the inflation lumen. A planar, sheet reinforcement member could be cut to shape when flat and subsequently bent into the desired tubular shape. To increase the strength of such a reinforcement member formed from sheet material it would be possible to join opposite sides of the member together at one or both ends of the member, that is, forwardly of the opening into the cuff and rearwardly of the opening to the inflation line. This would make the slot along the reinforcement more difficult to open by applying lateral pressure so would make the shaft more resistant to crushing and kinking. Various alternative forms of reinforcement are possible that allow the tube to have sufficient flexibility while strengthening the shaft against crushing and kinking.

The shaft is completed by an outer layer 30 of the same silicone material as the inner layer 20 or it could be a different grade of the same material. Different materials could be used providing they were compatible with the inner layer material or could be joined using an intervening material. This outer layer 30 is deposited to overlie the reinforcement element 25 and the rib 22 and provide a smooth outer surface for the shaft 10 with a circular section and to retain the reinforcement element 25 in place. The outer layer 30 could be formed by any conventional technique such as overmoulding or dipping. Instead having two separate layers, the shaft could be formed by a single layer overmoulded about the reinforcement member.

The inflation lumen 16 is blocked at the patient end 11 of the shaft 10 and a lateral, radial, or side opening 17 into the inflation is skived or otherwise formed from the outer surface of the shaft at a location that lies within the sealing cuff 13. The inflation tube 18 is joined to the inflation lumen 16 at the opposite, machine end of the shaft. Assembly operations also include steps of attaching the connector 14 and the flange 15.

The arrangement described enables a tube to be provided that is both reinforced against crushing and kinking and that has a cuff inflation lumen or other elongate member enclosed within its wall thickness so that the outer surface can be smooth and uninterrupted.

The reinforcement element need not extend along the entire length of the tube. In some tracheostomy tubes it may be preferable for the tube to be reinforced only along that part of its length that extends through the tracheostomy stoma. A short region at the patient end of the tube could be left unreinforced to provide a soft tip. The rear end of the tube could be left unreinforced to make it easier to insert and retain a tapered coupling. The invention could also have application to tubes other than tracheal tubes having an elongate member such as a gas sampling or suction lumen, or a cable for video imaging or sensing. Cuffed tubes include, for example, urethral catheters and vascular dilatation catheters.

The invention claimed is:

1. A medico-surgical tube comprising:
a shaft including an inner layer;
an elongate member providing or in the form of a lumen extending within a wall of the inner layer along a substantially straight line extending parallel to the axis of the shaft; the tube also including
a preformed reinforcement member extending along at least one part of the length of the shaft and wound around the inner layer along the at least one part of the length of the shaft, the reinforcement member having a plurality of loops extending around the circumference of the inner layer of the shaft up to but without crossing the elongate member provided along the inner layer; and
an outer layer overlying the reinforcement member to provide a smooth outer surface for the shaft.

2. The medico-surgical tube according to claim 1, wherein the reinforcement member includes two sets of loops extending around the shaft in opposite senses and extending up to the elongate member from opposite sides.

3. The medico-surgical tube according to claim 2, wherein the loops of one set are wider than the loops of the other set.

4. The medico-surgical tube according to claim 1, wherein the reinforcement member is of a metal wire.

5. The medico-surgical tube according to claim 1, wherein the wall of the shaft is of silicone.

6. The medico-surgical tube according to claim 1, wherein the tube includes an inflatable cuff towards its patient end, and that the elongate member is an inflation lumen opening into the cuff at one end.

7. The medico-surgical tube according to claim 6, wherein the tube is a tracheal tube and the inflatable cuff is a sealing cuff.

* * * * *